United States Patent [19]

Rosemeyer et al.

[11] Patent Number: 5,830,664
[45] Date of Patent: Nov. 3, 1998

[54] METHOD FOR THE DETECTION OF TARGET NUCLEIC ACID

[75] Inventors: Viola Rosemeyer, Wavre; Rudolf Seibl, Penzberg, both of Germany

[73] Assignee: Boehringer Mannheim GmbH, Mannheim, Germany

[21] Appl. No.: 503,058

[22] Filed: Jul. 17, 1995

[30] Foreign Application Priority Data

Jul. 16, 1994 [DE] Germany .......................... 44 25 264.1
Sep. 2, 1994 [DE] Germany .......................... 44 31 269.5

[51] Int. Cl.$^6$ .............................. C12Q 1/68; C12P 19/34; C07H 21/04; C07H 21/02
[52] U.S. Cl. ................................. 435/6; 435/91.2; 435/5; 435/91.1; 536/24.3; 536/24.32; 536/24.33; 536/23.1
[58] Field of Search ................................ 536/24.3–24.33, 536/23.1; 435/6, 5, 91.2, 91.1

[56] References Cited

U.S. PATENT DOCUMENTS

| | | | |
|---|---|---|---|
| 5,200,314 | 4/1993 | Urdea ........................................... | 435/6 |
| 5,232,829 | 8/1993 | Longiaru et al. ............................ | 435/6 |
| 5,422,253 | 6/1995 | Dahlberg et al. ..................... | 435/91.53 |
| 5,518,901 | 5/1996 | Murtagh ................................. | 435/91.2 |
| 5,573,914 | 11/1996 | Love ........................................... | 435/6 |

FOREIGN PATENT DOCUMENTS

A 72686   9/1991   Australia .
0 455 517 A1   11/1991   European Pat. Off. .

OTHER PUBLICATIONS

PCT International Publication No. WO 91/17264 published Nov. 14, 1991.
*BioTechniques*, "Probe Amplifier System Based on Chimeric Cycling Oligonucleotides", vol. 9, No. 2 (1990), pp. 142–147.

*Primary Examiner*—W. Gary Jones
*Assistant Examiner*—Dianne Rees
*Attorney, Agent, or Firm*—Nikaido Marmelstein Murray & Oram LLP

[57] ABSTRACT

Method for the sensitive detection of a target nucleic acid by hybridization with a probe nucleic acid. The latter contains a part which can hybridize with the target nucleic acid and a nucleic acid-specific part which does not hybridize with the target nucleic acid. The method further comprises cleavage of the probe nucleic acid, hybridization of a cleavage product of the probe nucleic acid containing the part that does not hybridize with the target nucleic acid with a matrix nucleic acid containing a part that can be hybridized with the cleavage product and a part that cannot be hybridized with the probe nucleic acid. The method also comprises the determination of the hybrid consisting of the cleavage product and the matrix nucleic acid and a reagent kit suitable for this purpose.

25 Claims, 8 Drawing Sheets

METHOD FOR THE DETECTION OF TARGET NUCLEIC ACID

Subject matter of the invention is a method for the sensitive detection of nucleic acids by hybridizing a probe nucleic acid with a target nucleic acid, digesting the hybridized part of the probe nucleic acid, and detecting the cleavage product. The invention also addresses a set of reagents suitable for this purpose.

Because of its specificity, the hybridization of nucleic acids has become a common tool in molecular analysis. Numerous different amplification methods have been developed with the objective of enhancing the frequently insufficient sensitivity of conventional detection methods in order to detect the probe molecules. The methods used for this purpose were based on the amplification of the actual target sequence or on target sequence-specific signal amplification. An example of such an amplification of the target sequence is the polymerase chain reaction as described in EP-A-0 200 362 where the two strands of the target nucleic acid are amplified in an in-vitro replication reaction. The temperature of the reaction is modified in cycles in order to denature the double-stranded target nucleic acid, enable hybridization with initiator molecules, subsequent DNA synthesis, and to repeat the steps.

The amplification of target sequences was, however, also accomplished by means of in-vitro transcriptions. An example for such a reaction is described in WO 88/10315. In this amplification, two primers are used one of which contains a promoter sequence. The primers are complementary to the different strands of the sequence to be amplified. EP-A-0 329 822 describes an improvement of this method where the double-stranded nucleic acid product, an intermediate product, is transcribed to produce ribonucleic acids which are digested in their hybrid form to allow yet another hybridization of the newly synthesized DNA with a promoter-containing primer molecule. By digesting the originally formed transcript, it is possible to form another double-stranded promoter-containing nucleic acid from each so-formed RNA molecule. These nucleic acids can then be used for another transcription start.

As opposed to the above-described methods, the target sequence-specific signal amplification does not amplify target nucleic acids, but is instead used for their specific identification. In order to accomplish this, a signal is amplified in dependency on the presence of the target sequence. A method of this type is described in WO 89/09284 and WO 89/10415. This cycling probe reaction (CPR) makes use of a labeled, chimeric DNA-RNA-DNA probe molecule which is hybridized with the target DNA molecule. The result of this hybridization is an RNA-DNA hybrid, which serves as a substrate for the RNAse H. As this enzyme specifically digests the RNA portion of the RNA-DNA hybrid, the probe molecule is cleaved and the resulting fragments dissociate from the target sequence due to the lower melting temperature. Subsequently, the target molecule can hybridize with another probe molecule and the cycle is repeated. The fragments of the probe molecule are detected via the label adhering to it.

Subject of the present invention is to increase the sensitivity of methods, where a target nucleic acid is hybridized with the probe molecule, and the digestion of the probe molecule is used to determine the target nucleic acid.

Subject matter of the invention is, hence, a method for the sensitive detection of a target nucleic acid A by means of
hybridizing the target nucleic acid A with a probe nucleic acid B which contains at least one part B1 which hybridizes with the target nucleic acid and a nucleic acid-specific part B2 which does not hybridize with the nucleic acid, cleaving the probe nucleic acid B in part B1, hybridizing a cleavage product B' of the nucleic acid B containing part B2 which does not hybridize with the target nucleic acid with a matrix nucleic acid C, containing a part C2 which can be hybridized with the cleavage product in part B2 and a part C1 which cannot be hybridized with part B1 of the probe nucleic acid, determining the hybrid of cleavage product B' and matrix nucleic acid C, and a reagent kit for implementing this method.

The method of the invention serves to detect a target nucleic acid A. This target nucleic acid can be of any desired origin, e.g. viral, bacterial, or cellular nucleic acids. They can be present in solution, suspension, but also fixed to a solid support or be present in cell-containing media, cytosmears, fixed cells, tissue sections, or fixed organisms. In a preferred manner, the nucleic acids are present in solutions.

Usually, the first step in a detection procedure is to make the target nucleic acid available with corresponding reagents. This includes changes of pH (basic), heat, repeating extreme temperature changes (freezing/thawing), changing the physiological growth condition (osmotic pressure), the effect of detergents, chaotropic salts or enzymes (e.g. proteases, lipases) either alone or in combination in order to release the nucleic acid. As the method of the invention is very sensitive and selective, it is also possible to detect small amounts of nucleic acid in the presence of other substances, e.g. proteins, cells, cell fragments, but also in the presence of non-target nucleic acids.

Suitable target nucleic acids are, for example, ribonucleic acids, or deoxyribonucleic acids. The nucleic acids may also be modified, for example in preceding treatment steps. Such treatment steps include digestion of nucleic acids, e.g. by means of a restriction enzyme. A particularly preferred target nucleic acid is a deoxyribonucleic acid (DNA).

The method of the invention is a special embodiment of a test based on a hybridization event, in particular the target sequence-specific signal amplification. The fundamentals of tests based on hybridization events are known to the expert in the field of nucleic acid diagnostics. Unless experimental details are described hereinafter, reference is made to the full contents of "Nucleic acid hybridization", edited by B. D. Hames and S. J. Higgins, IRL Press, 1986, e.g. in chapters 1 (hybridization Strategy), 3 (Quantitative Analysis of Solution Hybridization) and 4 (Quantitative Filter Hybridization), Current Protocols in Molecular Biology, Ed. F. M. Ausubel et al., J. Wiley and Son, 1987, and Molecular Cloning, Ed. J. Sambrook et al., CSH 1989. Other known methods include the preparation of labeled nucleoside triphosphates, as described in EP-A-0 324 474, the chemical synthesis of modified and non-modified oligonucleotides, the cleavage of nucleic acids with restriction enzymes, the selection of hybridization conditions to achieve a certain specificity which depends on the extent of the complementarity between the nucleic acids to be hybridized, on the GC contents and the lengths, as well as the synthesis of nucleic acids from nucleoside triphosphates with the aid of polymerases, and, optionally, the use of so-called primers.

A label as understood in the invention includes a direct or indirectly detectable group L. Directly detectable groups are, for example, radioactive ($^{32}$p), colored, or fluorescent groups or metal atoms. Indirectly detectable groups are, for example, immunologically or enzymatically active compounds, such as antibodies, antigens, haptens or enzymes, or enzymatically active partial enzymes. These are detected in a subsequent reaction or reaction sequence. Particularly preferred are haptens. When haptens are used as labels on nucleoside triphosphates, they are generally particularly suitable as substrates of polymerases and for a subsequent reaction with a labeled antibody to the hapten or the haptenized nucleoside. Such nucleoside triphosphates are, for example, bromium nucleoside triphosphate or digoxigenin-, digoxin-, biotin- or fluorescein-coupled nucleoside triphosphates. Particularly suitable are the steroids mentioned in EP-A- 0 324 474 and their detection. For further details on the incorporation of nucleic acids, refer to EP-A-0 324 474.

Possible nucleoside triphosphates (NTP) are ribo (rNTP) or deoxyribonucleoside triphosphates (dNTP).

Possible molecules for the probe nucleic acids B are those which contain two parts B1 and B2 connected to one another. Part B1 is characterized in that it can be hybridized with the target nucleic acid or at least a part thereof To achieve this, this part is sufficiently complementary. Moreover, part B1 must allow cleavage when present in a hybridized form with the target nucleic acid. Cleavage is in this context understood to be the separation of part B1 in two or more pieces that are no longer connected to one another, while the target nucleic acid is not cleaved. Part B1 may therefore contain ribonucleotide or abasic sequences. In the preferred case, part B1 contains two or more monoribonucleotide units connected to one another in a conventional manner, while the part of the target nucleic acid, which is complementary thereto, is a deoxyribonucleic acid. In this case, cleavage of probe nucleic acid B in part B1 can be accomplished in that the formed hybrid is brought into contact with RNAse H. If abasic sequences are present, digestion can be accomplished by means of AP endonucleases.

At least a portion of the hybridizable part B1 is digested. This results in a cleavage product B' which contains the nucleic acid-selective part B2 that does not hybridize with the target nucleic acid and, possibly, portions of part B1 which have been originally hybridized with the target nucleic acid.

The conditions for the hybridization of the target nucleic acid with the probe nucleic acid are preferably selected to just allow a specific hybridization of the probe nucleic acid with the target nucleic acid while a non-specific hybridization of the probe nucleic acid with another nucleic acid of the sample which is not to be detected is prevented. The fragments resulting from the cleavage of the probe nucleic acid, including cleavage product B', are shorter than the original probe nucleic acids and will no longer be able to form a stable hybrid with a target nucleic acid under the selected conditions. They will, hence, release the target nucleic acid A under the selected conditions.

Cleaving the probe nucleic acid may also lead to different fragments B' which contain either only part B2 or also remains of part B1. This depends on the conditions applied.

A nucleic acid-specific part of a nucleic acid is understood to be a sequence which can hybridize with another sequence than the target nucleic acid, where by specific hybridization occurs under the selected conditions, i.e. there is no hybridization with further nucleic acids present in the reaction mixture that is relevant for the procedure. Typical nucleic acid-specific parts are part B2 of the probe nucleic acid and part C2 of the matrix nucleic acid.

The nucleic acid-specific part B2 of the probe nucleic acid which does not hybridize with the target nucleic acid must satisfy the condition that it be not digested under the conditions applying to the target sequence-specific digestion of part B1. Moreover, it has to be able to hybridize with the matrix oligonucleotide which will be defined hereinafter. The sequence of part B2 may principally be selected as desired. What must be taken into consideration is that the hybridization of cleavage product B' with the matrix oligonucleotide becomes more difficult in case of a complementarity with the target nucleic acid. This will most likely reduce the sensitivity as compared to the optimal case. Moreover, it should be avoided that the probe molecule does tend to form partial double strands. B2 can also be a ribonucleic acid, a deoxyribonucleic acid or a modified nucleic acid. In case hybridizable part B1 contains a ribonucleic acid and cleavage is achieved by means of RNAse, part B2 is preferably not a ribonucleic acid that can be cleaved under these conditions in a preferred manner, it is a deoxyribonucleic acid. However, B2 may also be a ribonucleic acid that is modified such that it can no longer be cleaved by an RNAse. Another option is the use of nucleic acid analogs which still exhibit the hybridization properties of a nucleic acid, but no longer have a phosphate-sugar chain part. Particularly suitable for this purpose are the PNA molecules described in WO 92/20702 or WO 86/05518. The condition that this part does not hybridize with the target nucleic acid refers in particular to the conditions applying to the hybridization of the probe nucleic acid with the target nucleic acid. In a preferred manner, part B2 is selected such that it does not hybridize with nucleic acids of the sample not to be detected. However, part B2 should contain a sequence able to hybridize with the matrix nucleic acid C. The conditions for the hybridization of the target nucleic acid with the probe nucleic acid and the matrix nucleic acid with the cleavage product B' can be selected as desired.

The matrix nucleic acid C in accordance with the invention contains a part C2 which can hybridize with cleavage product B' and, especially, its nucleic acid-specific part B2 or a part thereof and with possibly present remains of B1. Suitable molecules for the matrix nucleic acid C are all those that allow a hybridization of this kind, i.e. nucleic acids consisting of natural nucleotide components; however, possible are also nucleic acid analogs consisting of components that are not naturally occurring or containing such components. Moreover, the matrix nucleic acid should be stable with respect to digestion under the selected conditions. In case cleavage of the probe nucleic acid is accomplished with RNAse, the particularly preferred matrix nucleic acid is a deoxyribonucleic acid. In addition to part C2, the matrix nucleic acid also has a part C1 which cannot hybridize with part B1 or present remains of part B1 of the probe nucleic acid. In a particularly preferred manner, this part C1 forms no stable hybrids with nucleic acids of the sample which are not to be detected or with the target nucleic acid itself under the selected conditions. It is preferred that part C1 be located in 5'-direction, beginning from part C2.

The matrix nucleic acid and the nucleic acid-specific part B2 are preferably selected such that the 5'-end of the cleavage product B' or the probe nucleic acid does not extend over the 3'-end of the matrix nucleic acid in their hybridized condition, if the incorporation of deoxynucleotides is to be detected in a subsequent reaction. This should prevent an enzymatic extension of the matrix nucleic acid. The same effect can be achieved by protecting the matrix nucleic acid at its 3'-end against enzymatic extension, e.g. by using a non-extendable mononucleotide.

It should be ensured in any case that the one or several cleavage products B' are able to hybridize with the matrix nucleic acid such that B' also hybridizes with the matrix nucleic acid at the end produced as a result of the cleavage and that part C1 of the matrix nucleic acid, when hybridized, still extends beyond the end of the cleavage product B' produced as a result of the cleavage.

In a subsequent step, the hybrid consisting of cleavage product B' and matrix nucleic acid C is determined. This determination is carried out such that possibly formed hybrids consisting of non-cleaved probe nucleic acid B and matrix nucleic acid C are not detected.

One of these options is based on the fact that cleavage product B' is extended with the aid of matrix nucleic acid C while the non-cleaved probe nucleic acid B is not extended. This is due to the above-described structural properties of the matrix nucleic acid not to hybridize with part B1 of the probe nucleic acid, while cleavage product B' hybridizes with the matrix nucleic acid. Cleavage product B' hybridizes in particular at the cleavage site (at the 3'-end of B') with C. Since the end of the matrix nucleic acid extends over the end of the cleavage product, nucleic acid which is complementary to the corresponding part of the matrix nucleic acid C may be attached in an extension reaction. There exist several variants of such an extension reaction. One variant is the attachment of mononucleotides with the aid of a DNA polymerase. In a preferred case, the mononucleoside triphosphates used are labeled, e.g. according to EP-A-0 324 474. If the mononucleoside triphosphates are not labeled, the formation of the extension product may be detected via separation by means of gel electrophoresis. In a particular embodiment, it is also possible to incorporate two different labels. In this case, one label may be used for the immobilization of the formed extension products and the other label serves for the detection. This is possible, for example, under the conditions described in EP-A-0 437 774.

In another embodiment, cleavage product B' serves as a primer in a polymerase chain reaction. When uncleaved, the probe nucleic acid B cannot act as a primer. In this case, the template of the PCR is the matrix nucleic acid C. When two different probe nucleic acids B are used, i.e. when they hybridize to different areas of the target nucleic acid that are complementary to one another, both primers can be generated in a PCR.

Another possibility of extending the cleavage product B' is the ligase reaction. In this case, an oligonucleotide is added, which hybridizes with the matrix nucleic acid such that a nick remains between the hybridized cleavage product B' and this oligonucleotide. This nick is then closed with the aid of a ligase.

In another preferred embodiment, part C1 of the matrix nucleic acid contains a transcription-or replication-initiating sequence. C1 preferably contains a promoter sequence. A functional complete promoter is formed during the matrix-controlled extension of cleavage product B1. After initiating transcription, which can only occur when the extension has actually taken place, the generation of cleavage products and, hence, the presence of the target nucleic acid can be detected. To achieve this, all reagents necessary for transcription are added to the reaction mixture, including a promoter-specific RNA polymerase, e.g. T7 RNA polymerase as well as ribonucleoside triphosphates of which a part preferably carries a label. The presence of the transcripts can then be used for the detection of the target nucleic acids. Reagents and conditions as necessary for in-vitro transcriptions are described in EP-A-0 329 822, for example. As compared to the first embodiment, the sensitivity is higher when the transcription is carried out subsequently.

The temperature for the method of the invention is selected such that the activities of the enzymes used are as optimal as possible while the hybridization conditions are at the same time selected so as to allow for sufficient specificity. When a non-thermostable RNAse is used, an advantageous temperature range is between 30° and 60°, the preferred temperature being 42°. When a thermostable RNAse is used, higher temperatures are also possible. The temperature used for the extension reaction also depends on the enzyme used for the extension. For the use of thermostable enzymes, e.g. Taq-DNA polymerase between 50° and 80° is preferred, and particularly preferred is between 60° and 70°. When a transcribing enzyme is used, the optimal temperature also depends on the activity of the enzyme, e.g. for T3, T7 and SP6 polymerase between 25° and 45°, particularly preferred 37°.

By increasing the chances of the enzymes, presence at the site of reaction, it is probably also possible to increase the conversion rate which in turn reduces the necessary reaction time or increases the sensitivity.

The matrix nucleic acid may also be a circular molecule. In this case, the use of an extension enzyme with strand displacement activity is preferred.

High flexibility and possible double labeling allow the use of the method on test strips or detection via coupling to beads and subsequent detection via flow cytometry or capillary electrophoresis.

In a possible embodiment, a part of the matrix nucleic acid contains a sequence which serves as a matrix for the synthesis of a replicable RNA, e.g. MDV 1 RNA or shorter sequences.

Principally, the probe nucleic acid and the matrix nucleic acid can be produced in accordance with known methods as soon as the sequence of their parts has been determined. If, in the preferred case, oligonucleotides with a length of less than 100 mononucleotide components are used, their synthesis according to common chemical methods (e.g. solid-phase synthesis according to Merrifield) is preferred. This also allows the easy synthesis of mixed oligonucleotides (RNAIDNA chimers). For larger nucleic acids, genetic engineering or chemical/enyymatic methods, as described in EP-A-325 970 are preferred. Part B1 has a preferred length of 12–35 nucleotides, Part B2 preferably 15–50, Part C1 preferably 10–100 and part C2 15–50.

The steps shown in the figures can be carried out successively while adding the respectively necessary reagents. Given a corresponding design of the components, all necessary components can also be added at the beginning of the reaction to have a simultaneously occurring process.

Figure 1:
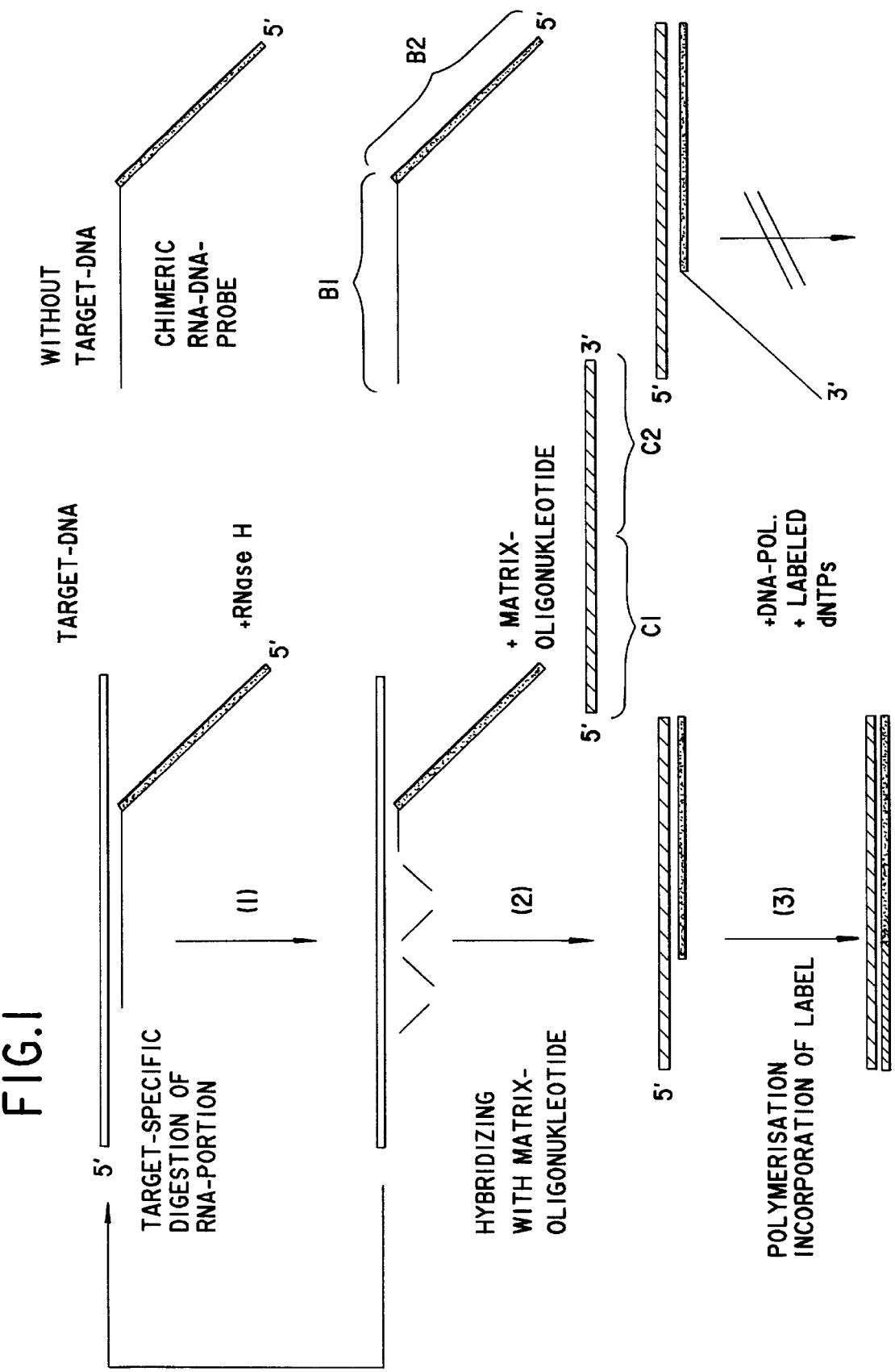
FIG. 1 shows a first embodiment of the invention based on the incorporation of non-radioactively labeled deoxyribonucleotide triphosphates with the aid of a DNA polymerase.

In a first preferred embodiment FIG. 1), a chimeric RNA-DNA or DNA-RNA-DNA probe molecule is added to a sample that contains a target DNA to allow hybridization. Due to the action of the RNAse H, the target sequence-specific RNA part of the probe is digested. Subsequently, suitable hybridization conditions are set and the matrix oligonucleotide together with the DNA polymerase as well as labeled and non-labeled deoxyribonucleoside triphosphates are added. The incorporation of labeled mononucleotides can be detected, for example, by separating the nucleic acids from the non-reacted labeled deoxyribonucleoside triphosphates. A direct, solid phase-based detection is possible when two differently labeled nucleotides are used. When there is no target DNA contained in the sample, the matrix oligonucleotide hybridizes only with the chimeric RNA-DNA probe molecule. An extension of the probe molecule is not possible as the 3'-end does not hybridize with the matrix oligonucleotide.

In a second preferred embodiment (FIG. 2), the target DNA contained in the sample is also hybridized to the chimeric RNA-DNA probe molecule or the DNA-RNA-DNA probe molecule. After digestion of the target sequence-specific RNA part due to the action of the RNAse H, the cleavage product is allowed to hybridize with an oligonucleotide which, at its 5'-end, extends over the end of the cleavage product and contains a single-stranded promoter sequence. By adding a DNA polymerase and deoxyribonucleotide triphosphates, the 3'-end of the cleavage product is extended to form a functional promoter. The resulting double-stranded nucleic acid is subject to transcription by RNA polymerase and nucleoside triphosphates. Promoter sequences for the various polymerases are known to the expert (e.g. Nucl. Acids Res. 12, 7035–7056 (1984)).

In a third embodiment (FIG. 8), the probe nucleic acid and the matrix nucleic acid are not separate molecules, but are linked to one another. To achieve this, one end of the matrix nucleic acid is attached to the end of part B2 of the probe nucleic acid which faces away from B1 so that part C2 and part B2 can hybridize forming a hair-pin structure, with parts B1 and C1 becoming the ends of this hair-pin molecule. Parts B2 and C2 can be linked in any desired way, for example, through a covalent link, preferably with the aid of mononucleotide units, for example, oligo-dA. To allow the hair-pin structure to form, it is recommended that a linker of 3 to 20 nucleotides or equivalents in length be provided between the hybridizable parts C2 and B2. In case that B2 is located at the 5'-end of the probe molecule, the link is provided between the 5'-end of B2 and the 3'-end of C2. The advantage of this embodiment is that the spatial vicinity of the hybridizing parts of the probe nucleic acid and the matrix nucleic acid enhances the reaction rate.

Figure 2:
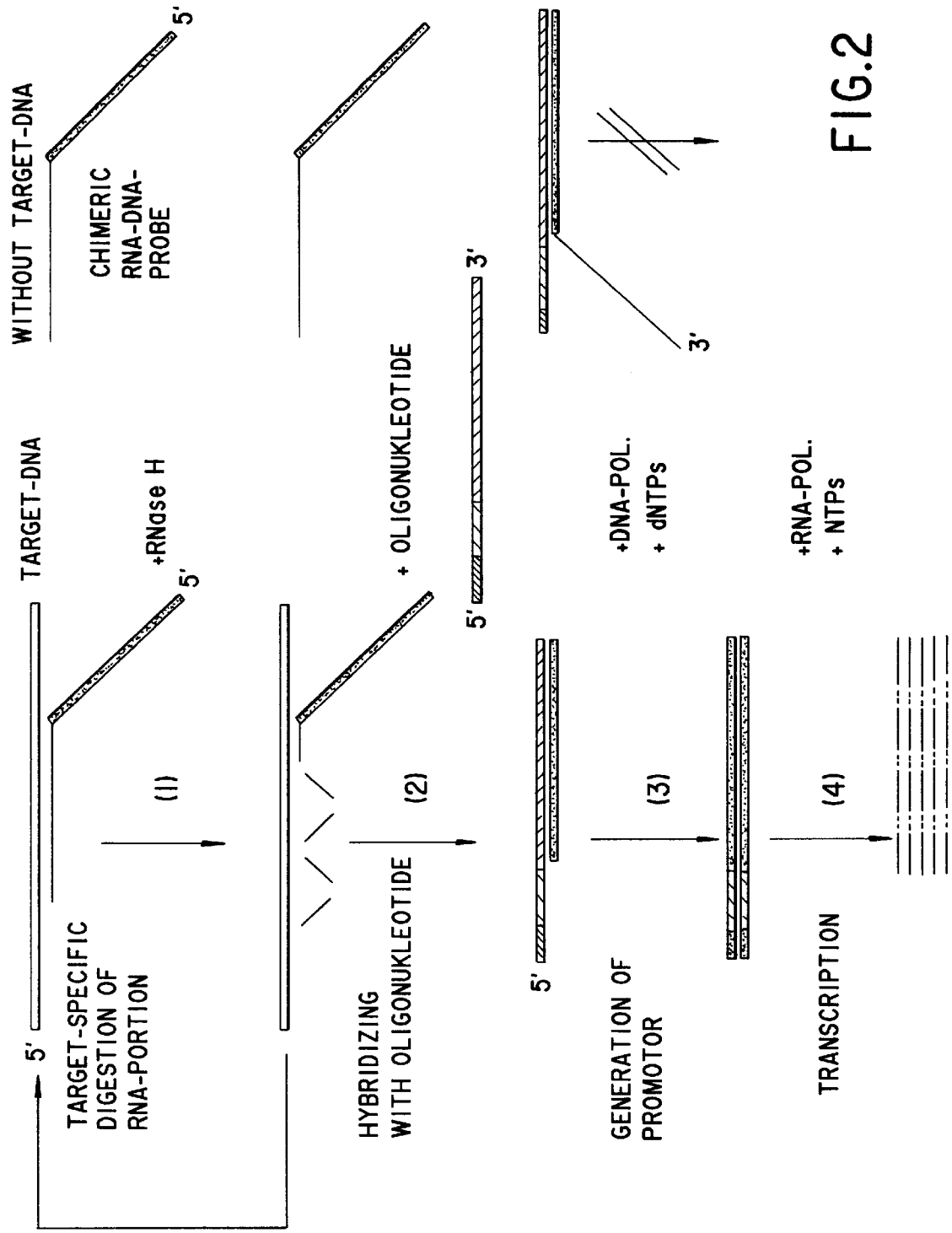
FIG. 2 is a diagrammatic demonstration of an embodiment where the matrix oligonucleotide contains a promoter sequence which is turned into a functional promoter followed by a transcription. The promoter sequence is represented in hatched lines.
Figure 8:
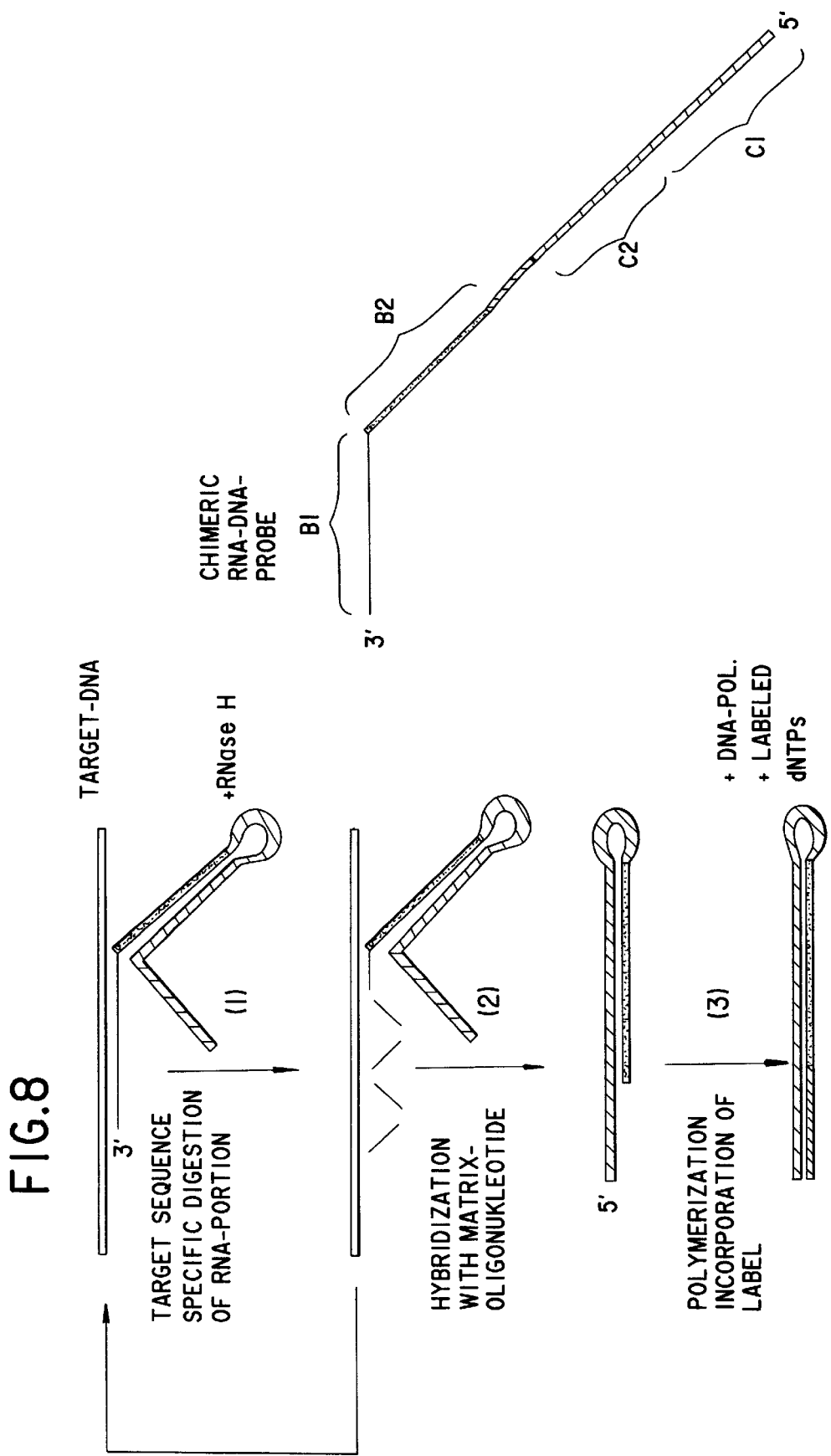
FIG. 8 is a diagrammatic demonstration of an embodiment where the probe nucleic acid and the matrix nucleic acid are connected to each other.

The description of the embodiment of FIG. 8 can be applied analogously to FIG. 2 (generation of a promoter).

An advantage of the method of the invention is that the probe nucleic acid B needs not to contain a label. This facilitates the synthesis of the probe nucleic acid, but has also the consequence that a background signal due to these labels cannot occur in a later detection reaction. In the method of the invention, a target sequence is not amplified. The risk of contamination with amplified molecules from previous experiments can, hence, be excluded. In the method of the invention, the product of the last reaction step is not used as a substrate for the next first reaction step. The reaction can therefore be easily controlled. A quantitative determination is facilitated by the fact that the amplification is essentially linear. On the other hand, the risk of obtaining false-positive results due to cross-contamination of originally negative samples with small amounts of actually positive samples with respect to the exponential amplification system is reduced. The method of the invention does not require technical equipment for a cyclic variation of the incubation temperature. The method of the invention is also in so far flexible that the use of two different non-radioactive labels according to EP-A-0 437 774 allows both binding to a solid phase as well as detection of the products. Since the continuation of the reaction steps depends entirely upon the specific hybridization of the probe molecule with the target sequence in the method of the invention, background signals generated by non-specific binding or persistence of non-hybridized probe molecules, as they occur, for example, during amplification with replicable ribonucleic acid sequences (Qβ replication), are not generated. As opposed to methods where two or more oligonucleotides of different sequences are made to react in one mixture, a non-specific reaction of the oligonucleotides, (as, for example, primer-dimers in the PCR) can be almost completely excluded in the method of the invention. The method of the invention can be carried out under non-stringent hybridization conditions. This also allows the detection of related sequences. When the assay is carried out under very stringent conditions, it is also possible to detect point mutations. Owing to the .fact that in the method of the invention, the detection does not require the detection of a labeled, truncated probe molecule in addition to the originally used labeled probe molecules, the use of gel electrophoresis methods for separating the molecules is avoided. The method can thus be automated and used in routine analysis procedures.

Another subject matter of the invention is a reagent kit for carrying out the above-mentioned detection reaction. This kit contains the probe nucleic acid B and, either separately or in the same container, the matrix nucleic acid C. In a preferred manner, the reagent kit also contains a buffer for the hybridization and digestion reactions and/or the extension reaction. In a particularly preferred manner, the kit contains detectably labeled mononucleoside triphosphates. If the reagents are provided in two different containers, the first container preferably contains the probe nucleic acid, an enzyme for carrying out the digestion reaction, and suitable buffers. In the second container, there is the matrix nucleic acid, at least one enzyme for carrying out the extension reaction with mononucleoside triphosphates, and a suitable buffer.

The following examples explain the invention in greater detail.

EXAMPLE 1

Method with incorporation of labeled mononucleotides

In the following description, upper case letters used in oligonucleotides describe deoxyribonucleotide units and lower case letters describe ribonucleotide units.

Procedure 1 pmol, 10 pmol or 100 pmol of the RNA-DNA probe molecule (LPRO3__19R: 5'-GATCGGACTGGAAGTAAT-ACGACTCACcgccgcgucgcagaagauc-3'(SEQ. ID. NO. 1) or LPR03__25R: 5'-GATCGGACTGGAAGTAATAC-GACTCACcgccgcgucgcagaagaucucaauc-3'(SEQ. ID NO. 2) were incubated with various amounts of the DNA to be detected (DHBV1: 5'-GATTGAGATCTTCTGCGACG-CGGCGGT-3'(SEQ. ID. NO. 3)) in a volume of 10 at 42° C. for 3 hours in buffer P2 (10 mM Hepes, 1 mM $MgCl_2$, pH 8.0) with 3 μg, BSA, 20 U RNasin and 4 U RNase H being added. Then 10 pmol of the matrix oligonucleotide TAQ (5'-ATTCCATGATTCATTGATTATTGTCGCGGCGGT-GAGTCGTATTACTTCCAGTCCGATC-3'(SEQ. ID. NO 4)) were added. The mixture was then heated up for 1 minute to 100° C. and immediately chilled on ice. For the polymerase reaction, 2 μl Taq buffer (10 mM Tris pH 8.3, 50 mM KCl, 1.5 mM $MgCl_2$, 0.1 mg/ml gelatin), the nucleotide mixture 1_3 (1 μM dATP, dGTP, dCTP, DIG-dUTP each (Boehringer Mannheim) and BIO-dUTP (Boehringer Mantheim)), 20 U RNasin, 1 U Taq-DNA polymerase and $H_2O$ were added to a final volume of 20 μl and incubated for 15 minutes at 60° C.

For the detection, the reaction mixtures were diluted to 210 μl with buffer D (10 mM HEPES (pH 8.0), 30 mM NaCl, 1 mM $MnCl_2$). The BIO-DIG-reaction synthesis products were immobilized in a streptavidin-coated microtiter plate (TRSA-SA-MTP, manufactured by MicroCoat) by pipetting 100 μl of the reaction mixture diluted with buffer D into s well of a SA-MTP prewashed with washing buffer (0.5% V/V Tween 20 in PBS (phosphate-buffered saline)). The MTP was incubated under shaking for 1 hour at 37° C. (Well-Warm, manufactured by Denley Instruments GmbH).

The MTP with the immobilized nucleic acid molecules was washed five times with 200 μl washing buffer. Then, 100 μl of the conjugate dilution (polyclonal <DIG>-S-$F_{ab}$-$POD_{poly}$ conjugate (Boehringer Mannheim GmbH), 200 mU/ml in conjugate buffer (100 MM sodium phosphate (pH 7.5), 0.9% (W/V) NaCl, 1% (W/V) Ralufon F4J or BSA Fraction V; the conjugate buffer was treated with DEPC sterile, filtered (0.2 μm filter, manufactured by Nalgene) and stored at 4° C.)) were added and incubated under identical conditions (1 h, 37° C.).

Non-bound conjugate molecules were removed by washing 5 times. Now 100 μl of the substrate solution (2,2'-azino-di-[3-ethylbenzthiazoline sulfate(6)], ABTS) were added per well. The color reaction took place at 37° C. under shaking. The O.D. of the converted ABTS at 405 nm was measured after brief shaking of the microtiter plate directly prior to the measurement with an ELISA reader (SLT) against a reference filter of 492 nm. The mean values of the duplicate determination were obtained after subtracting the zero value (ABTS only) (SLT Easy-Base Version 4.01).

Sensitivity

Figure 3:
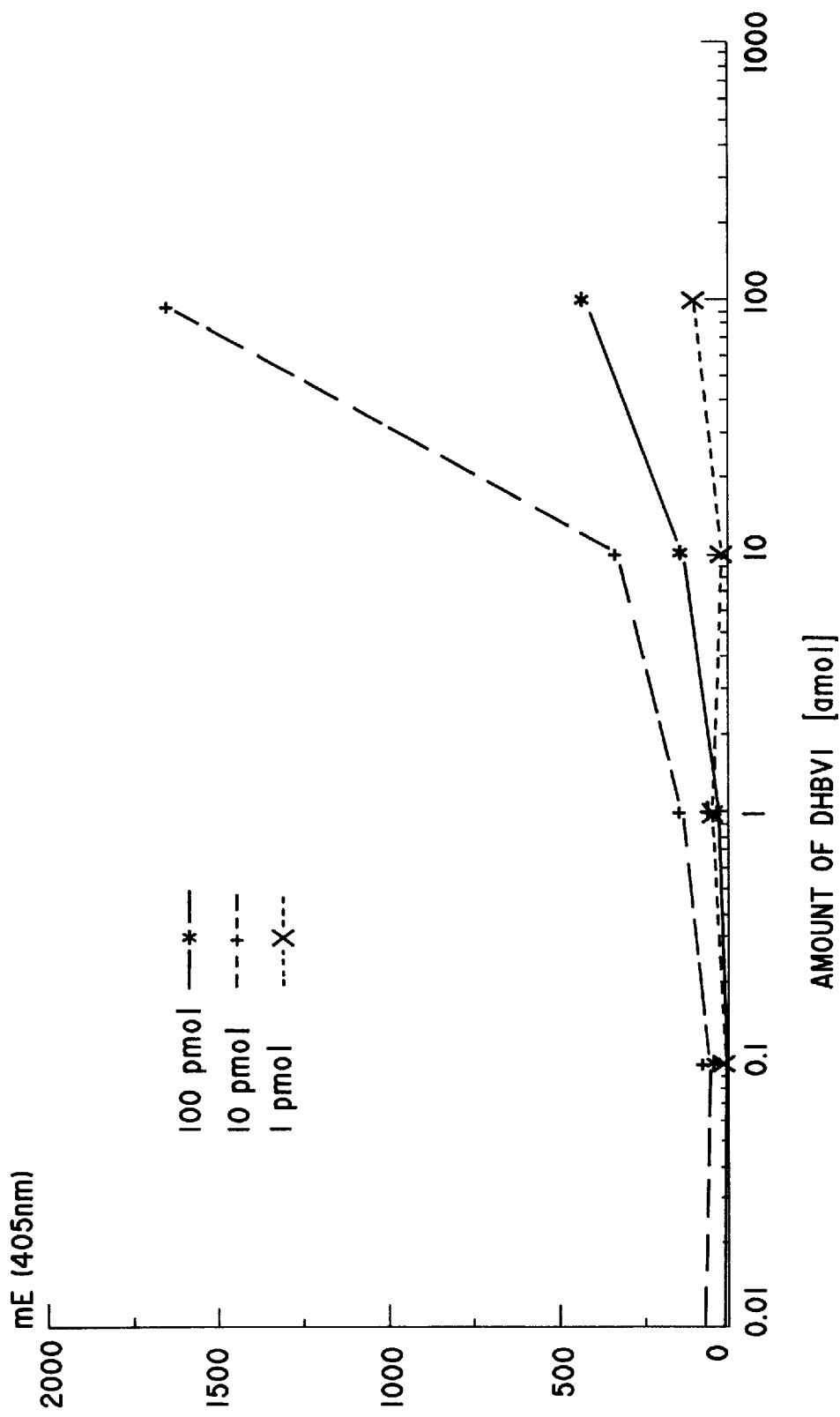
FIG. 3 shows the sensitivity of the method according to FIG. 1 in dependency on the amount of probe nucleic acid with 10 pmol matrix nucleic acid being used for each reaction mixture.

In order to determine the sensitivity of the method the matrix nucleic acid was used at a concentration of 10 pmol in the above-described reaction mixture. The result is shown in FIG. 3. The curves of FIG. 3 show that under the reaction conditions selected (10 pmol matrix oligonucleotide, amount of RNase H, incubation volume, incubation temperature, etc.), the most sensitive detection was obtained with 10 pmol of probe molecule. The use of only 1 pmol probe nucleic acid is likely to limit the first step of the reaction, hybridization and digestion. When 100 pmol of probe nucleic acid are used, not all digested probe molecules can hybridize with matrix oligonucleotides and thus be extended. It can, hence, be stated that under the selected conditions, the highest sensitivity is obtained with 10 pmol probe nucleic acid per mixture and that 10 amol of target nucleic acid can be detected under these conditions. This detection limit is by a factor of approximately 10 lower than the method according to WO 89/10415 which detects 0.1 fmol of nucleic acid under equivalent conditions.

Temperature dependency

Figure 4:
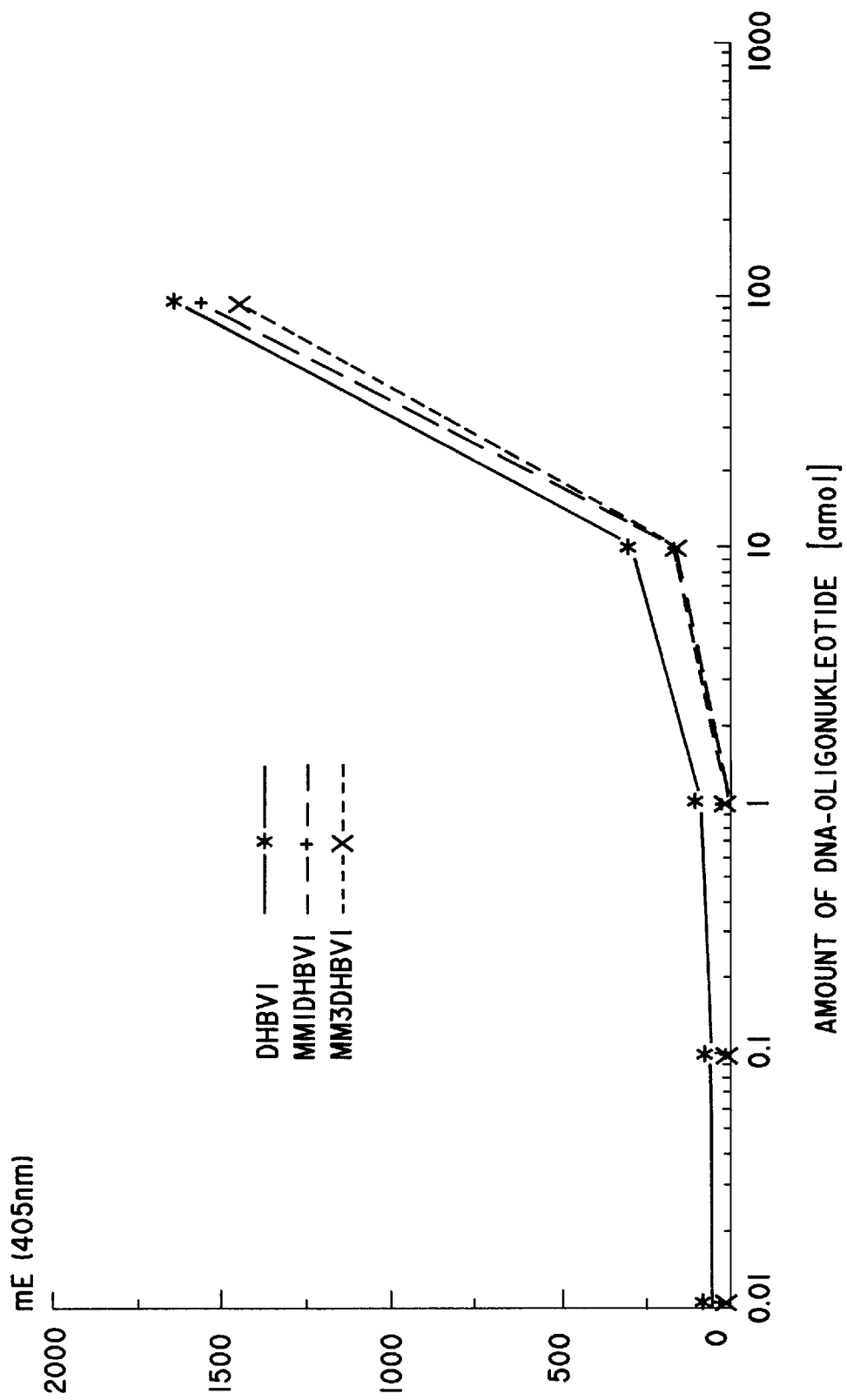
FIGS. 4–6 show the specificity of a detection of DNA sequences with the method according to FIG. 1 in dependency upon the incubation temperature of the hybridization and digestion reactions (42° C., 50° C., and 56° C.).
Figure 5:
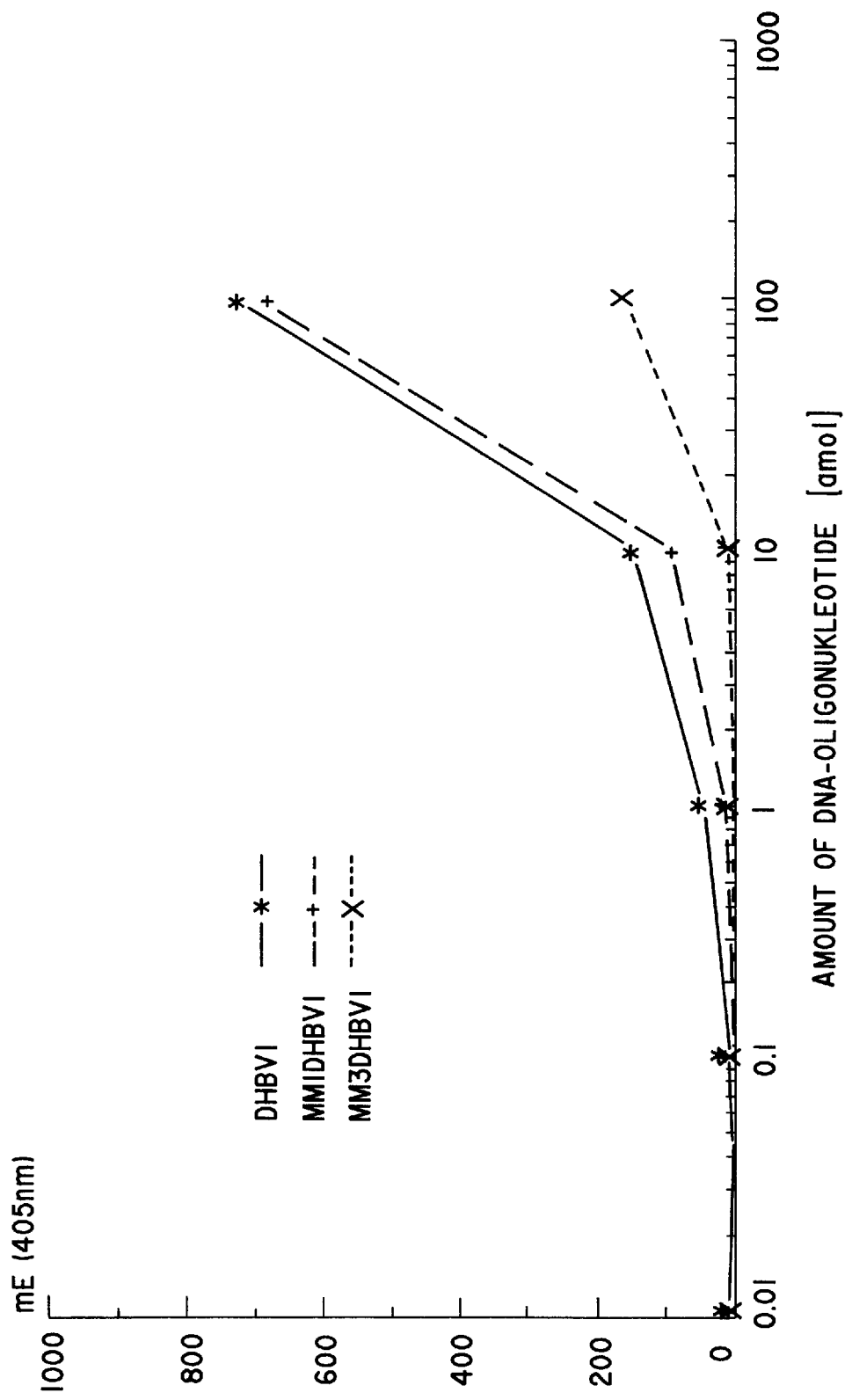
Figure 6:
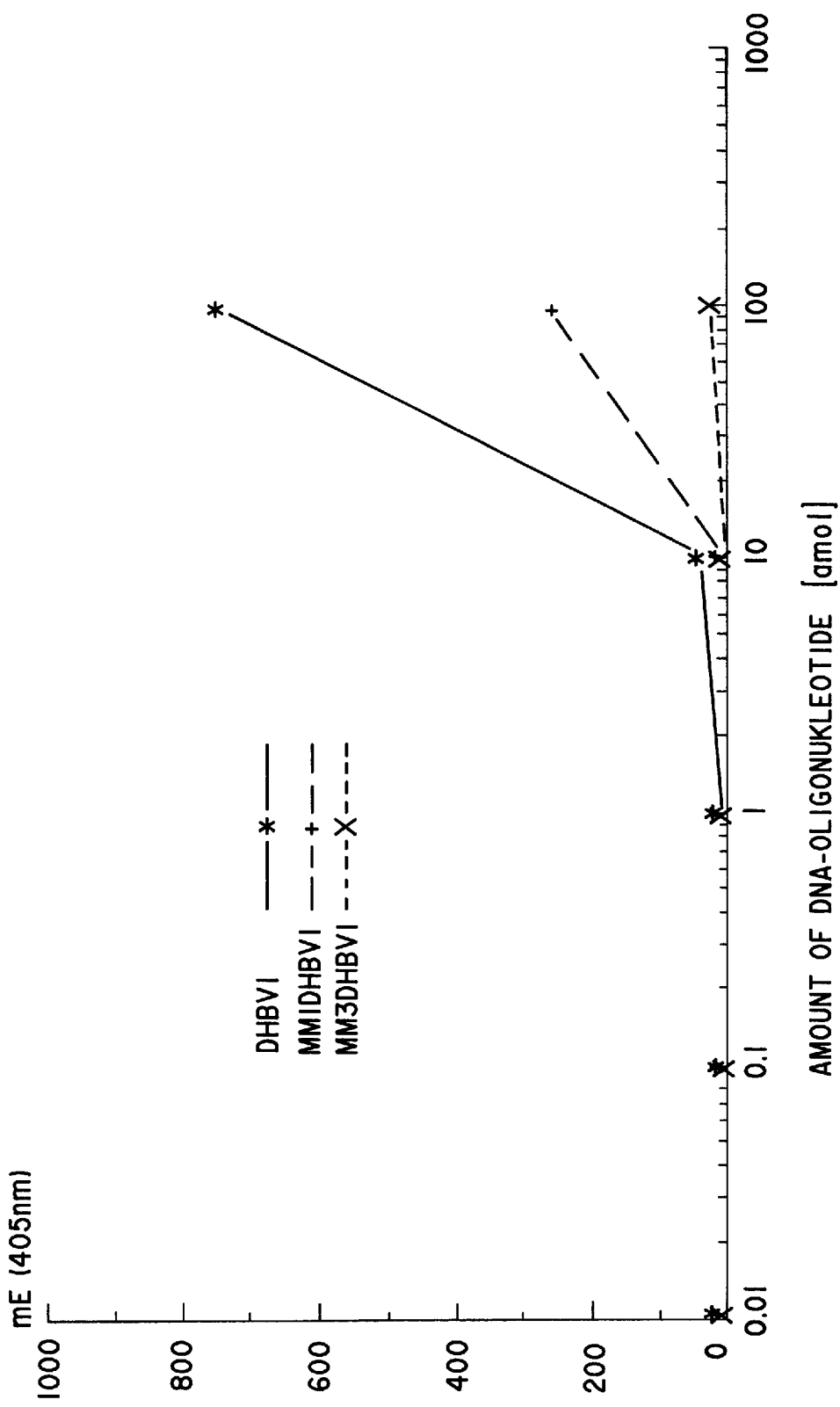

In order to describe the temperature dependency of the method of the invention of example 1, 10 pmol probe nucleic acid were used for each assay and incubated in the presence of 0.01 amol up to 100 amol of target nucleic acid with RNAse H at 42° C. (FIG. 4), 50° C. FIG. 5) and 56° C. (FIG. 6). All subsequent polymerase reactions were carried out at 60° C. Analysis was made after a 30-minute incubation with ABTS. The probe molecule used was HBV 1 or MM 1 DHBV 1 (5'-GATTGAGATCTTATGCGA-CGCGGCGGT-3', SEQ. ID. No. 7) (one base mismatch) or MM 3 DHBV 1 (5'-GATTGAGATCTCACGCGA-CGCGGCGGT-3', SEQ. ID. No. 8) (three base mismatches). At an incubation temperature of 42° C. for the digestion reaction, the experiment led to almost identical curves and, hence, to a poor sequence specificity of the method of the invention. When the stringency was increased by raising the incubation temperature to 50° C., the perfectly complementary oligonucleotide HBV 1 and the oligonucleotide forming one base mismatch produced similar curves for the detection. However, there was a reduced sensitivity as compared to the incubation temperature of 42° C., the reason being the incomplete digestion of the RNA portion. The oligonucleotide forming three base mismatches generated significantly lower signals, which was due to the lower hybridization rate under the more stringent conditions. The highest specificity was obtained at an incubation temperature of 56° C.. 100 amol DHBV 1 generated a clear signal, 100 amol MM 1 DHBV 1 led to a lower O.D., and 100 amol MM 3 DHBV 1 could not be detected. This shows that the method of the invention allows a sequence-specific detection of nucleic acids. In series of 3×3, 10 pmol probe nucleic acid with different amounts (0.01 amol to 100 amol) of the perfectly complementary target nucleic acid DHBV 1, the target nucleic acid MM 1 HBV 1 producing a central base mismatch and the target nucleic acid MM 3 DHBV 1 producing three central base mismatches were used. The first three series were incubated at 42° C., the second three series at 50° C. and the third three series at 56° C. The negative controls for each series were reaction mixtures without target nucleic acids. The polymerase reaction was in all cases carried out at 60° C. The values measured in a subsequent detection reaction in a streptavidin-coated microfilter plate are represented in FIGS. 4–6.

EXAMPLE 2

Method with formation of a functional promoter

Figure 7:
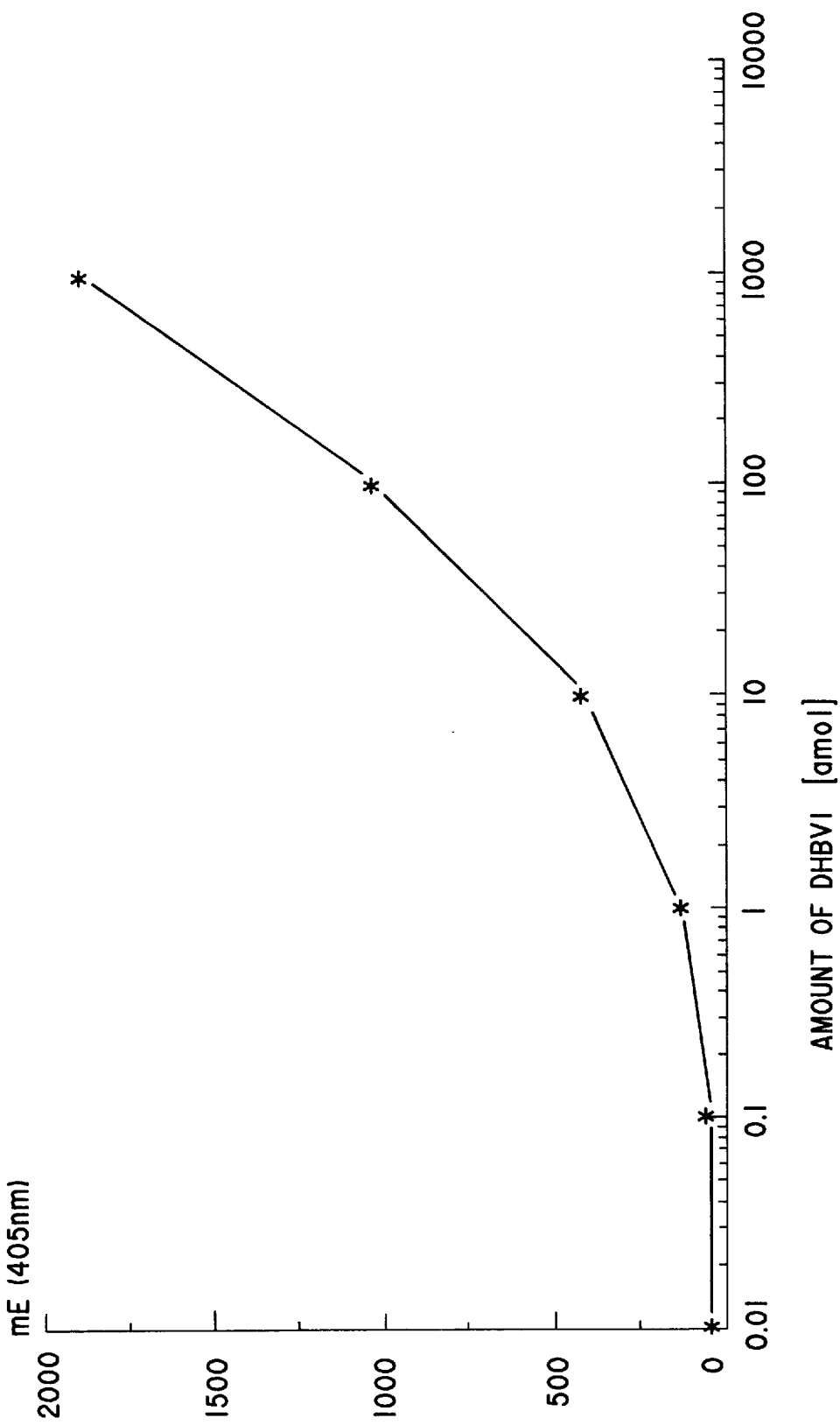
FIG. 7 shows the sensitivity of the detection according to the method of FIG. 2.

Procedure 10 pmol of RDCPTAQ (5'-ATGATAGTTGATGATAGTTGGATATcgccgccu-ggcagaagauc-3'(SEQ. IID. NO. 5)) were incubated with different amounts of DHBV1 (5'-GATTGAGATCTTCT GCGACGCGGCGGT-3'(SEQ. I.D. NO. 9)), 0.01 amol to 10 fmol) in a volume of 10 μl with RNase H for 1 h at 42° C., P2 buffer (10 mM Hepes, 1 mM $MgCl_2$, pH 8.0), with 3 μg BSA, 20 U RNasin and 4 U RNase H being added. The negative control used was a reaction mixture without DHBV1. Then 10 pmol of QAT2 (5'-GATCGGACTGGAAGTAATACGACTCACTAT-AGGGCGGCGA TATCCAACTATCATCAACTATCAT-3' (SEQ. I.D. NO. 6)), 2 Taq buffer (10 mM Tris pH 8.3, 50 mM KCl, 1.5 mM $MgCl_2$, 0.1 mg/ml gelatin) and 1 mM dATG, dGTP, dCTP and dTTP were added to each mixture, and the polymerase reaction catalyzed by the Taq-DNA polymerase was carried out for 15 min at 60° C. in a reaction volume being increased to 20 μl. Subsequently, 3 μl transcription buffer (40 mM Tris pH 7.9, 6 mM $MgCl_2$, 10 mM DTT, 2 mM spermidin), 20 U RNasin, 0.5 μl 1% Triton X-100 and 500 U T7-RNA polymerase and the nucleotide mixture CP1 with DIG- and BIO-UTP (9.84 μM ATP, 4.92 μM GTP, 2.46 μM CTP, 3.28 μM UTP, 820 nM DIG-UTP and 820 nM BIO-UTP) were added. The total volume now was 30 μl. Incubation was carried out for 2 hours at 37° C. For the detection reaction, all mixtures were diluted to 210 μl using buffer D and 100 μl were pipetted into one well of an SA-MRP. The detection was carried out with <DIG>-POD$_{poly}$ and ABTS (Boehringer Mannheim) as described in Example 1, the measurements are shown in FIG. 7.

As can be gathered from the curves, 1 amol of the target sequence DHBV 1 could be detected under the selected reaction conditions. This detection limit is by a factor of approximately 10 lower than the method with the incorporation of labeled deoxyribonucleotides (Example 1) where 10 amol of target nucleic acid were detected under equivalent conditions.

We claim:

1. A method for the detection of a target nucleic acid A, comprising:
   (a) hybridizing the target nucleic acid A with a probe nucleic acid B, wherein said probe nucleic acid B has a 5'-end and a 3'-end, and wherein said probe nucleic acid B comprises a part B1 which hybridizes with at least a part of the target nucleic acid A and a part B2 which does not hybridize with the target nucleic acid A;
   (b) cleaving said hybridized probe nucleic acid B to produce a cleavage product B', wherein said cleavage product 3' has a 5'-end and a 3'-end, and wherein said cleavage product B' comprises said part B2;
   (c) hybridizing said cleavage product B' with a matrix nucleic acid C, wherein said nucleic acid C has a 5'-end and a 3'-end, and wherein said matrix nucleic acid C comprises a part C2 which hybridizes with at least a part of said cleavage product B' and a part C1 which does not hybridize with said part B1 of said probe nucleic acid B; and
   (d) determining the presence of the hybrid formed in step (c) to detect said target nucleic acid A.

2. The method according to claim 1, wherein said determining step (d) comprises extending said cleavage product B' forming a nucleic acid which is complementary to part C1 of said matrix nucleic acid C.

3. The method according to claim 2, wherein said extending step comprises attaching mononucleotides to said cleavage product B'.

4. The method according to claim 3, wherein said mononucleotides are non-radioactively labeled.

5. The method according to claim 2, wherein said extending step comprises using said cleavage product B' as a primer and said matrix nucleic acid C as a template in a polymerase chain reaction.

6. The method according to claim 2, wherein said extending step comprises:
   (i) hybridizing an oligonucleotide with said matrix nucleic acid C such that space remains between said cleavage product B' and said oligonucleotide; and
   (ii) closing the space using a ligase reaction.

7. The method according to claim 2, wherein said part C1 of said matrix nucleic acid C comprises a promoter sequence.

8. The method according to claim 1, wherein said part C2 of said matrix nucleic acid C has a 5'-end and a 3'-end, and wherein said part C1 of said matrix nucleic acid C is located at the 5'-end of said part C2.

9. The method according to claim 2, wherein said matrix nucleic acid C comprises a group connected to the 3'-end of said matrix nucleic acid C which inhibits an extension of said matrix nucleic acid C at said 3'-end.

10. The method according to claim 2, wherein the 5'-end of said cleavage product B' is identical to the 5'-end of said probe nucleic acid B, and the 5'-end of said cleavage product B' does not extend over the 3'-end of said matrix nucleic acid C in a hybridization complex.

11. The method according to claim 2, wherein in said hybridizing step (c) the nucleotide at the 3'-end of said cleavage product B' hybridizes with said matrix nucleic acid C.

12. The method according to claim 1, wherein after said cleaving step (b) the part B1 is released from the target nucleic acid A and said hybridizing step (a) is repeated with a further probe nucleic acid B.

13. The method according to claim 1, wherein said target nucleic acid A is present in solution before step (a).

14. The method according to claim 13, wherein non-target nucleic acids are also present in solution.

15. The method according to claim 1, wherein said part B1 of said probe nucleic acid B is 12–35 nucleotides in length, said part B2 of said probe nucleic acid B is 15–50 nucleotides in length, said part C1 of said matrix nucleic acid C is 10–100 nucleotides in length and said part C2 of said matrix nucleic acid C is 15–50 nucleotides in length.

16. The method according to claim 1, wherein said probe nucleic acid B and said matrix nucleic acid C are linked before step (a).

17. A reagent kit for the detection of a target nucleic acid comprising:
   a probe nucleic acid B comprising a part B1 which hybridizes with at least a part of the target nucleic acid and a part B2;
   a matrix nucleic acid C comprising a part C2 which hybridizes with at least a part of said part B2 and a part C1 which does not hybridize with said part B1 of said probe nucleic acid B; and
   a reagent capable of cleaving said probe nucleic acid B when said probe nucleic acid B is bound to the target nucleic acid, wherein said reagent is incapable of cleaving said probe nucleic acid or the target nucleic acid alone.

18. The reagent kit according to claim 17, further comprising:
   an enzyme for the matrix-dependent synthesis of nucleic acids; and
   a buffer.

19. The reagent kit according to claim 18, wherein said reagent is RNase H, and said enzyme for the matrix-dependent synthesis of nucleic acids is a DNA polymerase.

20. The reagent kit according to claim 17, further comprising detectably labeled mononucleoside triphosphates.

21. The reagent kit according to claim 17, further comprising an RNA polymerase.

22. The reagent kit according to claim 17, further comprising:
- a first container;
- a second container;
- a cleaving enzyme;
- a first and second buffer; and
- an enzyme for the matrix-dependent synthesis of nucleic acids, wherein said probe nucleic acid B, said cleaving enzyme and said first buffer are in said first container, and wherein said matrix nucleic acid C, said enzymes for the matrix-dependent synthesis of nucleic acids and said second buffer are in said second container.

23. The reagent kit according to claim 17, wherein the part B2 does not hybridize with the target nucleic acid.

24. The method according to claim 1, wherein said 3'-end of said probe nucleic acid B does not hybridize with said matrix nucleic acid C in a hybridization complex between the nucleic acids B and C.

25. The method according to claim 1, wherein said nucleic acid C is unable to undergo enzymatic extension from its 3'-end.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: nucleic acid ( i x ) FEATURE:
        ( A ) NAME/KEY: misc_feature
        ( B ) LOCATION: 1..46
        ( D ) OTHER INFORMATION: /note= "Nucleotides 1-27 are deoxyribonucleotides, and nucleotides 28-46 are ribonucleotides."

( x i ) SEQUENCE DESCRIPTION: SEQ ID NO:1:

GATCGGACTG GAAGTAATAC GACTCACCGC CGCGUCGCAG AAGAUC              46

( 2 ) INFORMATION FOR SEQ ID NO:2:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: nucleic acid ( i x ) FEATURE:
        ( A ) NAME/KEY: misc_feature
        ( B ) LOCATION: 1..52
        ( D ) OTHER INFORMATION: /note= "Nucleotides 1-27 are deoxyribonucleotides, and nucleotides 28-52 are ribonucleotides."

( x i ) SEQUENCE DESCRIPTION: SEQ ID NO:2:

GATCGGACTG GAAGTAATAC GACTCACCGC CGCGUCGCAG AAGAUCUCAA UC       52

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

GATTGAGATC TTCTGCGACG CGGCGGT                                27

( 2 ) INFORMATION FOR SEQ ID NO:4:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

ATTCCATGAT TCATTGATTA TTGTCGCGGC GGTGAGTCGT ATTACTTCCA GTCCGATC 58

( 2 ) INFORMATION FOR SEQ ID NO:5:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: nucleic acid ( i x ) FEATURE:
        ( A ) NAME/KEY: misc_feature
        ( B ) LOCATION: 1..45
        ( D ) OTHER INFORMATION: /note= "Nucleotides 1-25 are
            deoxyribonucleotides, and nucleotides 26-44 are
            ribonucleotides."

( x i ) SEQUENCE DESCRIPTION: SEQ ID NO:5:

ATGATAGTTG ATGATAGTTG GATATCGCCG CCUGGCAGAA GAUC 44

( 2 ) INFORMATION FOR SEQ ID NO:6:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

GATCGGACTG GAAGTAATAC GACTCACTAT AGGGCGGCGA TATCCAACTA TCATCAACTA 60

TCAT 64

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

GATTGAGATC TTATGCGACG CGGCGGT 27

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

-continued

```
GATTGAGATC TCACGCGACG CGGCGGT                                                    27
```

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

```
GATTGAGATC TTCTGCGACG CGGCGGT                                                    27
```